(12) United States Patent
Wu et al.

(10) Patent No.: US 10,130,264 B2
(45) Date of Patent: Nov. 20, 2018

(54) POLYSILOXANE ELASTOMER CONTAINING LIQUID CRYSTAL LATERAL CHAIN, AND SMART WATCH MADE FROM THE SAME

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Xiaojuan Wu, Beijing (CN); Jian Wang, Beijing (CN)

(73) Assignees: BOE TECHNOLOGY GROUP CO., LTD., Beijing (CN); BEIJING BOE OPTOELETRONICS TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/141,185

(22) Filed: Apr. 28, 2016

(65) Prior Publication Data

US 2017/0052395 A1    Feb. 23, 2017

(30) Foreign Application Priority Data

Aug. 20, 2015   (CN) .......................... 2015 1 0515754

(51) Int. Cl.
| | |
|---|---|
| *C09K 19/40* | (2006.01) |
| *A61B 5/01* | (2006.01) |
| *C09K 19/36* | (2006.01) |
| *C08G 77/38* | (2006.01) |
| *C09K 19/32* | (2006.01) |
| *G02F 1/01* | (2006.01) |
| *G04G 17/00* | (2013.01) |

(52) U.S. Cl.
CPC ................ *A61B 5/01* (2013.01); *C08G 77/38* (2013.01); *C09K 19/36* (2013.01); *C09K 19/408* (2013.01); *C09K 2019/323* (2013.01); *G02F 1/0147* (2013.01); *G04G 17/00* (2013.01)

(58) Field of Classification Search
CPC .................................. G02F 1/13; A61M 1/00
See application file for complete search history.

(56) References Cited

U.S. PATENT DOCUMENTS

2004/0120684 A1* 6/2004 Ishibashi ............ C09K 11/7734
  385/141
2006/0251365 A1* 11/2006 Brewer ............. G02F 1/133524
  385/116

FOREIGN PATENT DOCUMENTS

CN    102643432 A  *  8/2012
CN    103980832 A  *  8/2014
(Continued)

OTHER PUBLICATIONS

Chinese Office Action dated Nov. 16, 2017.

*Primary Examiner* — Chanceity N Robinson
(74) *Attorney, Agent, or Firm* — Dilworth & Barrese, LLP.; Michael J. Musella, Esq.

(57) ABSTRACT

A polysiloxane elastomer containing liquid crystal lateral chain, and a smart watch made therefrom are disclosed. The polysiloxane elastomer containing liquid crystal lateral chain includes a polysiloxane backbone chain and a lateral chain formed by a liquid crystalline monomer and connected with the polysiloxane backbone chain, wherein the polysiloxane backbone chain is crosslinked by a crosslinking agent.

3 Claims, 3 Drawing Sheets

(56) References Cited

FOREIGN PATENT DOCUMENTS

CN 103992445 A 8/2014
CN 104166275 A 11/2014

\* cited by examiner

POLYSILOXANE ELASTOMER CONTAINING LIQUID CRYSTAL LATERAL CHAIN, AND SMART WATCH MADE FROM THE SAME

TECHNICAL FIELD

Embodiments of the present disclosure relate to a polysiloxane elastomer containing a liquid crystal lateral chain, and a smart watch made from the same.

BACKGROUND

With the development of mobile technology, many traditional electronic products also begin to be added with mobile-related functions. For example, watches, which in the past can only be used for viewing time, now may also be connected into internet through smart phones or home networks to display incoming call information, news, weather information, etc. A smart watch is a watch with a built-in intelligent system or a loaded smart phone system to be connected into a network, thereby achieving a multiple of functions and being synchronized with the calls, messages, emails, photos, music, etc. in the phone. With the increase of people's living standards, the requirements for health care and other functions of smart watches are increasing. Some smart watches have achieved the functions of viewing heart rate, walk step number, calorie burn condition, etc., in real time and transferring local data through software to fitness service software. Temperature measurement function is an important function for health status monitoring. Currently, the temperature measurement module in a smart watch is generally composed of a temperature sensor and a control unit; connected with the control main board of the smart watch; and supplied with operating electric power by a power supply circuit of the smart watch.

The temperature measurement module in current smart watch may increase the power consumption of the smart watch and decrease the cruising ability of the smart watch. At the same time, when the energy of the watch is exhausted, this function would be lost, which is unfavorable for human body status monitoring.

SUMMARY

An embodiment of the present disclosure provides a polysiloxane elastomer containing a liquid crystal lateral chain, which comprises a polysiloxane backbone chain and a lateral chain formed by a liquid crystalline monomer and connected with the polysiloxane backbone chain, wherein the polysiloxane backbone chain is crosslinked by a crosslinking agent.

In some embodiments, for example, the crosslinking agent contains at least two terminal carbon-carbon double bonds and the liquid crystalline monomer contains at least one carbon-carbon double bond.

In some embodiments, for example, the crosslinking agent is binaphthyl diol p-alkenyloxybenzoate with the following structural formula:

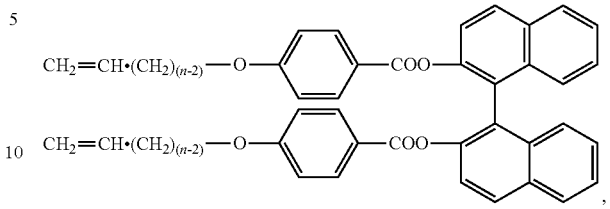

wherein n is an integer of 2-15.

In some embodiments, for example, the liquid crystalline monomer is cholesterol p-alkenyloxybenzoate with the following structural formula:

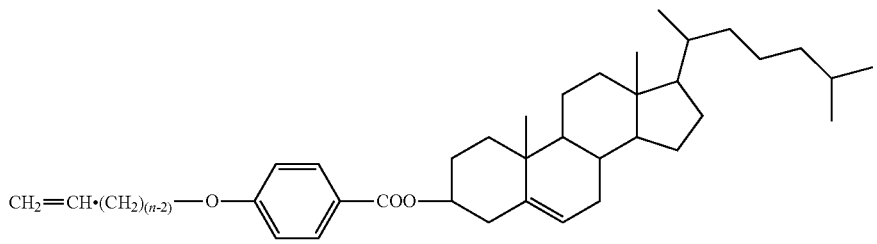

wherein n is an integer of 2-15.

In some embodiments, for example, the polymethylhydrosiloxane has the following structural formula:

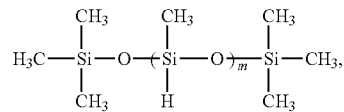

wherein m is an integer of 4-30.

An embodiment of the present disclosure further provides a method for preparing the polysiloxane elastomer containing a liquid crystal lateral chain, comprising: dissolving the polysiloxane into a solvent to obtain a polysiloxane solution; adding an crosslinking agent, a liquid crystalline monomer and a catalyst into the polysiloxane solution to obtain a reactant mixture; and reacting the reactant mixture under reflux under an inert atmosphere to obtain the polysiloxane elastomer containing a liquid crystal lateral chain.

An embodiment of the present disclosure further provides use of the polysiloxane elastomer containing a liquid crystal lateral chain in an automatic body temperature sensing device.

An embodiment of the present disclosure further provides an automatic body temperature sensing device, which comprises the polysiloxane elastomer containing a liquid crystal lateral chain.

An embodiment of the present disclosure further provides a thermosensitive liquid crystal display module, comprising a transparent thermal non-thermal-conductive material layer, a material layer containing a polysiloxane elastomer containing a liquid crystal lateral chain, and a thermal conductive material layer, which are arranged from top to bottom.

An embodiment of the present disclosure further provides a method for preparing a thermosensitive liquid crystal display module, comprising: arranging the material layer containing a polysiloxane elastomer containing a liquid crystal lateral chain on the surface of the thermal conductive material layer; and covering with a transparent thermal non-thermal-conductive material layer.

An embodiment of the present disclosure further provides use of the thermosensitive liquid crystal display module in a smart watch.

An embodiment of the present disclosure further provides a smart watch comprising the thermosensitive liquid crystal display module. For example, the smart watch comprises a dial and a watch band, and the watch band is arranged with the thermosensitive liquid crystal display module thereon.

BRIEF DESCRIPTION OF THE DRAWINGS

In order to illustrate the technical solutions of the embodiments of the present disclosure more clearly, the figures of the embodiments are briefly described below. Apparently, the figures described below merely relate to some embodiments of the present disclosure rather than are limitative of the present disclosure.

Figure 1:
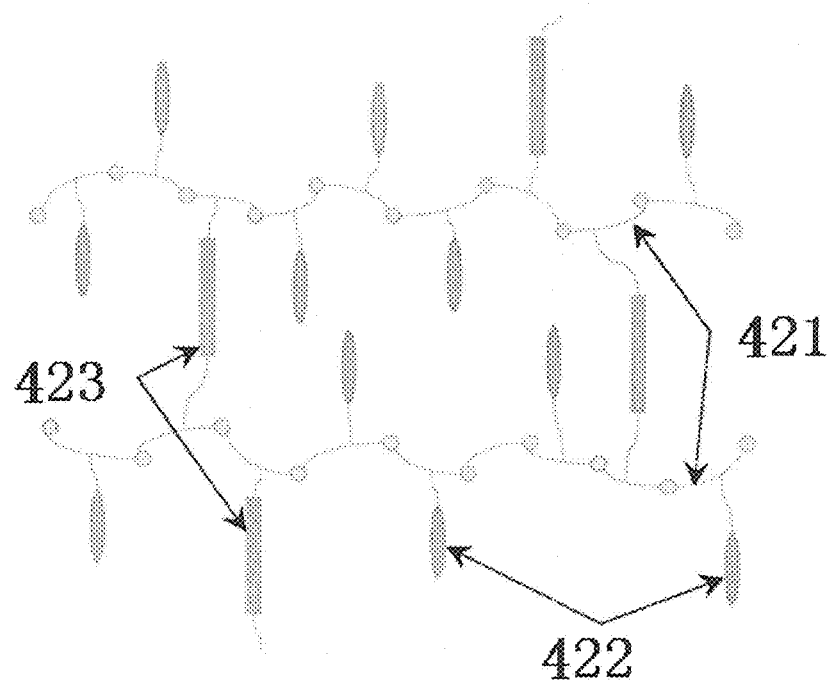
FIG. 1 is a structural schematic view of the polysiloxane elastomer containing a liquid crystal lateral chain of the embodiment of the present disclosure.

The description of reference signs:
1. dial; 2. watch band; 3. watch band buckle; 4, thermosensitive liquid crystal display module; 41. transparent thermal non-thermal-conductive material layer; 42. material layer of the polysiloxane elastomer containing a liquid crystal lateral chain; 43. thermal conductive material layer; 421. polymethylhydrosiloxane backbone chain; 422. liquid crystalline monomer; 423. crosslinking agent.

DETAILED DESCRIPTION

To make the object, technical solutions, and advantages of the embodiments of the present disclosure clearer, the technical solutions of the embodiments of the present disclosure will be described below in a clearer and more complete way with reference to the figures of the embodiments of the present disclosure. Apparently, the embodiments described are only part, rather than all of the embodiments of the present disclosure. Based on the embodiments of the present disclosure described, all other embodiments obtained by a person of ordinary skills in the art without paying inventive work fall into the scope of protection of the present disclosure.

In the present application, the term "liquid crystal lateral chain" means a lateral chain formed by a liquid crystalline monomer, specifically a liquid crystalline monomer, i.e. a liquid crystal molecule, which is bonded with a polysiloxane, such as polymethylhydrosiloxane, backbone chain. The liquid crystal lateral chain is formed by bonding the liquid crystalline monomer on the polysiloxane, such as polymethylhydrosiloxane, backbone chain, such as by grafting reaction.

The present disclosure comprises the following embodiments:

Embodiment 1

A polysiloxane elastomer containing a liquid crystal lateral chain, comprising a polysiloxane backbone chain and a lateral chain formed by a liquid crystalline monomer and connected with the polysiloxane backbone chain, wherein the polysiloxane backbone chain is crosslinked by a crosslinking agent.

Embodiment 2

The polysiloxane elastomer containing a liquid crystal lateral chain as defined according to embodiment 1, wherein the crosslinking agent contains at least two terminal carbon-carbon double bonds and the liquid crystalline monomer contains at least one carbon-carbon double bond Embodiment 3

The polysiloxane elastomer containing a liquid crystal lateral chain as defined according to embodiment 1, wherein the polysiloxane is polymethylhydrosiloxane, and the crosslinking agent and the liquid crystalline monomer are connected on the polysiloxane by hydrosilylation reaction.

Embodiment 4

The polysiloxane elastomer containing a liquid crystal lateral chain as defined according to embodiment 3, wherein the crosslinking agent is binaphthyl diol p-alkenyloxybenzoate with the following structural formula:

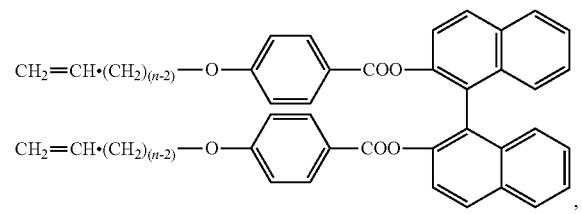

wherein n is an integer of 2-15.

Embodiment 5

The polysiloxane elastomer containing a liquid crystal lateral chain as defined according to embodiment 4, wherein the liquid crystalline monomer is cholesterol p-alkenyloxybenzoate with the following structural formula:

$CH_2\!=\!CH\!\cdot\!(CH_2)_{(n-2)}$—O—⟨benzene⟩—COO—⟨cholesteryl⟩, wherein n is an integer of 2-15.

Embodiment 6

The polysiloxane elastomer containing a liquid crystal lateral chain as defined according to embodiment 5, wherein the polymethylhydrosiloxane has the following structural formula:

$$H_3C-\underset{\underset{CH_3}{|}}{\overset{\overset{CH_3}{|}}{Si}}-O\!-\!\!\left(\underset{\underset{H}{|}}{\overset{\overset{CH_3}{|}}{Si}}-O\right)_{\!m}\!\!-\underset{\underset{CH_3}{|}}{\overset{\overset{CH_3}{|}}{Si}}-CH_3,$$

wherein m is an integer of 4-30.

Embodiment 7

The polysiloxane elastomer containing a liquid crystal lateral chain as defined according to embodiment 3, wherein the grafting ratio of the crosslinking agent to the liquid crystalline monomer grafted on the polymethylhydrosiloxane backbone chain is 1:(1/9-9).

Embodiment 8

The polysiloxane elastomer containing a liquid crystal lateral chain as defined according to embodiment 6, wherein the number m of the Si—H bonds in the polymethylhydrosiloxane is 6; the olefin carbon chain length n in the liquid crystalline monomer is 10; the olefin carbon chain length n in the crosslinking agent is 10; and the grafting ratio of the crosslinking agent to the liquid crystalline monomer is 1:3.

Embodiment 9

The polysiloxane elastomer containing a liquid crystal lateral chain as defined according to embodiment 6, wherein the number m of the Si—H bonds in the polymethylhydrosiloxane is 8; the olefin carbon chain length n in the liquid crystalline monomer is 8; the olefin carbon chain length n in the crosslinking agent is 8; and the grafting ratio of the crosslinking agent to the liquid crystalline monomer is 1:1.

Embodiment 10

The polysiloxane elastomer containing a liquid crystal lateral chain as defined according to embodiment 6, wherein the number m of the Si—H bonds in the polymethylhydrosiloxane is 10; the olefin carbon chain length n in the liquid crystalline monomer is 12; the olefin carbon chain length n in the crosslinking agent is 12; and the grafting ratio of the crosslinking agent to the liquid crystalline monomer is 1:2.

Embodiment 11

A method for preparing the polysiloxane elastomer containing a liquid crystal lateral chain as defined according to embodiment 1, comprising: dissolving the polysiloxane into a solvent to obtain a polysiloxane solution; adding an crosslinking agent, a liquid crystalline monomer and a catalyst into the polysiloxane solution to obtain a reactant mixture; and reacting the reactant mixture under reflux under an inert atmosphere to obtain the polysiloxane elastomer containing a liquid crystal lateral chain.

Embodiment 12

The method as defined according to embodiment 11, wherein the polysiloxane is polymethylhydrosiloxane; the crosslinking agent is binaphthyl diol p-alkenyloxybenzoate; the liquid crystalline monomer is cholesterol p-alkenyloxybenzoate; and the catalyst is chloroplatinic acid/tetrahydrofuran.

Embodiment 13

Use of the polysiloxane elastomer containing a liquid crystal lateral chain as defined according to embodiment 1 in an automatic body temperature sensing device.

Embodiment 14

An automatic body temperature sensing device, comprising the polysiloxane elastomer containing a liquid crystal lateral chain as defined according to embodiment 1.

Embodiment 15

A thermosensitive liquid crystal display module, comprising a transparent thermal non-thermal-conductive material layer, a material layer containing a polysiloxane elastomer containing a liquid crystal lateral chain as defined according to embodiment 1, and a thermal conductive material layer, which are arranged from top to bottom.

Embodiment 16

The thermosensitive liquid crystal display module as defined according to embodiment 15, wherein the transparent thermal non-thermal-conductive material layer is made of Teflon plastics; and the thermal conductive material layer is made of at least one of those selected from thermal conductive silicon sheet, thermal conductive graphene and composite silicone oil thermal conductive grease.

Embodiment 17

A method for preparing the thermosensitive liquid crystal display module as defined according to embodiment 15, comprising: arranging the material layer containing a polysiloxane elastomer containing a liquid crystal lateral chain on the surface of the thermal conductive material layer; covering with a transparent thermal non-thermal-conductive material layer; and extruding to be formed.

Embodiment 18

A smart watch comprising the thermosensitive liquid crystal display module as defined according to embodiment 9.

Embodiment 19

The smart watch as defined according to embodiment 18, further comprising a dial and a watch band, wherein the watch band is provided with the thermosensitive liquid crystal display module thereon.

Embodiment 20

The smart watch as defined according to embodiment 19, wherein the smart watch comprises at least one thermosensitive liquid crystal display module; and the thermosensitive liquid crystal display module is located on the left side, on the right side or on both left and right sides of the dial.

Figure 6:
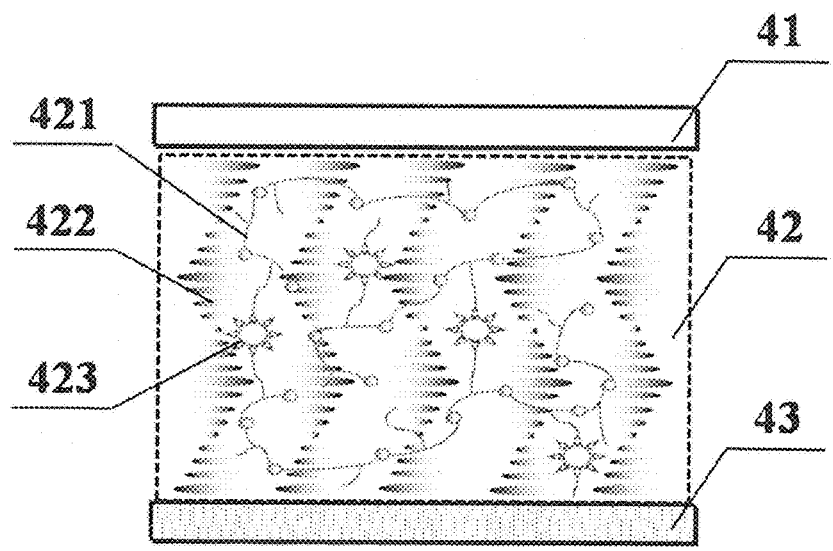
FIG. 6 is a structural schematic view of the thermosensitive liquid crystal display module.

In an embodiment of the present disclosure, a crosslinking agent and a liquid crystalline monomer are grafted onto a polymethylhydrosiloxane backbone chain to obtain a liquid crystal elastomer, as shown in FIG. 6. The selective reflected wavelength thereof can be changed with temperature, thereby changing color thereof. The use of the thermosensitive liquid crystal display module prepared therefrom in, such as, a smart watch may achieve the function of automatic human body temperature sensing without power consumption.

Figure 7:
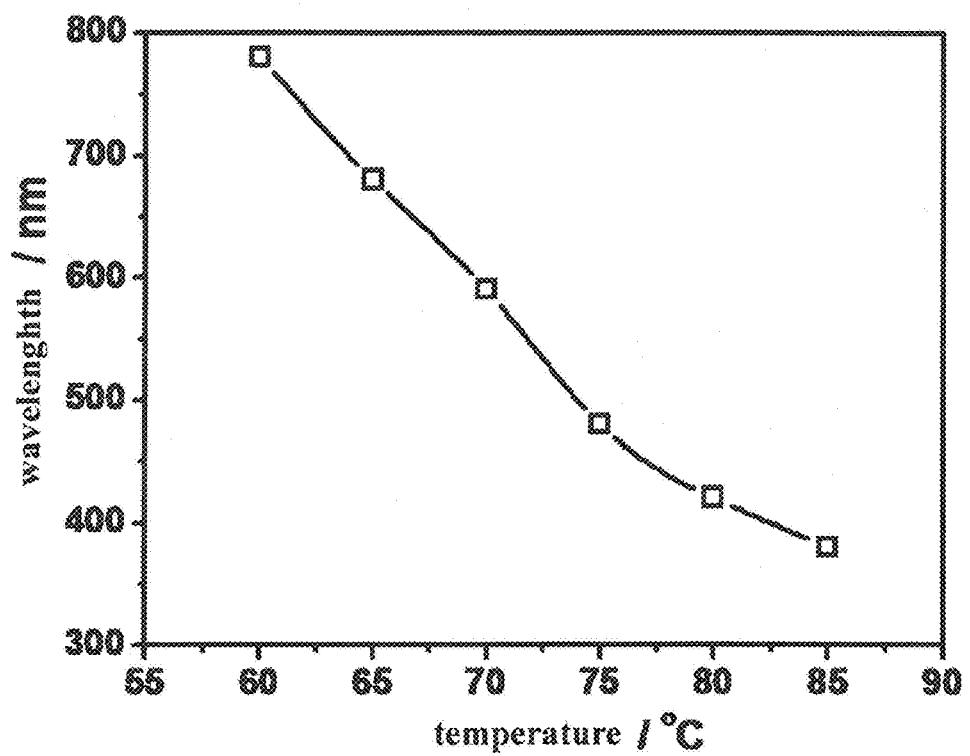
FIG. 7 is a temperature-dependent curve of the reflected wavelength of the polysiloxane elastomer containing a liquid crystal lateral chain.

FIG. 7 shows a temperature-dependent curve of the reflected wavelength of the polysiloxane elastomer containing a liquid crystal lateral chain. In the liquid crystal elastomer, m is 6; n is 4; and the grating ratio of the crosslinking agent to the liquid crystalline monomer is 5:4. As seen from this figure, with the increase of the temperature, the reflected wavelength of the polysiloxane elastomer containing a liquid crystal lateral chain is gradually decreased. When m is fixed, the phase transition temperature, phase state and reflected wavelength of the polysiloxane elastomer containing a liquid crystal lateral chain can be adjusted by changing the value of n and the grating ratio of the crosslinking agent to the liquid crystalline monomer; When n is fixed, the phase transition temperature, phase state and reflected wavelength of the polysiloxane elastomer containing a liquid crystal lateral chain can be adjusted by changing the value of m and the grating ratio of the crosslinking agent to the liquid crystalline monomer; When the grating ratio of the crosslinking agent to the liquid crystalline monomer is fixed, the phase transition temperature, phase state and reflected wavelength of the polysiloxane elastomer containing a liquid crystal lateral chain can be adjusted by changing the values of m and n.

By adjusting the backbone chain length in the polysiloxane elastomer containing a liquid crystal lateral chain, the molecular structure and ratio of the liquid crystal element, and the molecular structure and ratio of the crosslinking agent, the reflected wavelength of the polysiloxane elastomer containing a liquid crystal lateral chain can be adjusted such that three states may be exhibited at 37° C.: 1) the glassy state, which is transparent; 2) cholesteric phase with a reflected wavelength outside the range of 350-780 nm, which displays no color and is transparent; or 3) cholesteric phase with a reflected wavelength in the range of 350-780 nm, which displays a visible light of a specific color at 37° C.; when the ambient temperature is higher than 37° C., both the glassy state and the cholesteric phase may reflected a visible light of another color because of the change of spiral twisting force in the elastomer.

As one embodiment of the present disclosure, when the number m of the Si—H bonds in the polymethylhydrosiloxane is 6; the olefin carbon chain length n in the liquid crystalline monomer is 10; the olefin carbon chain length n in the crosslinking agent is 10; and the grafting ratio of the crosslinking agent to the liquid crystalline monomer is 1:3, the obtained polysiloxane elastomer containing a liquid crystal lateral chain has a glass transition temperature of 37° C., and is in a cholesteric phase above the glass transition temperature. For example, the selective reflected wavelength thereof at 38° C. is 780 nm and therefore a red visible light may be displayed.

As one embodiment of the present disclosure, when the number m of the Si—H bonds in the polymethylthydrosiloxane is 8; the olefin carbon chain length n in the liquid crystalline monomer is 8; the olefin carbon chain length n in the crosslinking agent is 8; and the grafting ratio of the crosslinking agent to the liquid crystalline monomer is 1:1, the obtained polysiloxane elastomer containing a liquid crystal lateral chain has a glass transition temperature of 30° C., and is in a cholesteric phase above the glass transition temperature. For example, the selective reflected wavelength thereof at 37° C. is 1000 nm, which is outside the visible light range of 350-780 nm, therefore no color is reflected and a transparent state is displayed; and the selective reflected wavelength thereof at 38° C. is 750 nm and therefore a red color is reflected.

As one embodiment of the present disclosure, when the number m of the Si—H bonds in the polymethylhydrosiloxane is 10; the olefin carbon chain length n in the liquid crystalline monomer is 12; the olefin carbon chain length n in the crosslinking agent is 12; and the grafting ratio of the crosslinking agent to the liquid crystalline monomer is 1:2, the obtained polysiloxane elastomer containing a liquid crystal lateral chain has a glass transition temperature of 28° C., and is in a cholesteric phase above the glass transition temperature. For example, the selective reflected wavelength thereof at 37° C. is 750 nm and therefore a red color is displayed; and the selective reflected wavelength thereof at 38° C. is 620 nm and therefore a green color is reflected.

An embodiment of the present disclosure further provides a method for preparing the above-mentioned polysiloxane elastomer containing a liquid crystal lateral chain, comprising: dissolving the polysiloxane into a solvent to obtain a polysiloxane solution; adding an crosslinking agent, a liquid crystalline monomer and a catalyst into the polysiloxane solution to obtain a reactant mixture; and reacting the reactant mixture under reflux under an inert atmosphere to obtain the polysiloxane elastomer containing a liquid crystal lateral chain. By using this method, a polysiloxane elastomer containing a liquid crystal lateral chain with a more perfect color change effect can be obtained.

An embodiment of the present disclosure further provides a use of the above-mentioned polysiloxane elastomer containing a liquid crystal lateral chain in an automatic body temperature sensing device; thereby achieve the function of automatic body temperature sensing without power consumption.

An embodiment of the present disclosure further provides a thermosensitive liquid crystal display module, comprising a transparent thermal non-thermal-conductive material layer, a material layer containing a polysiloxane elastomer containing a liquid crystal lateral chain, and a thermal conductive material layer, which are arranged from top to bottom, as shown in FIG. 6. The transparent thermal non-thermal-conductive material protects the thermosensitive polysiloxane elastomer containing a liquid crystal lateral chain from the influence of the external temperature. Meanwhile, the color change of the polysiloxane elastomer containing a liquid crystal lateral chain can be sensed by human eyes. The thermal conductive material may transfer human body temperature to the thermosensitive polysiloxane elastomer containing a liquid crystal lateral chain to sense the body temperature and respond to the body temperature.

An embodiment of the present disclosure further provides a method for preparing the thermosensitive liquid crystal display module, comprising: arranging the material layer containing a polysiloxane elastomer containing a liquid crystal lateral chain on the surface of the thermal conductive material layer; covering with a transparent thermal non-thermal-conductive material layer; and extruding to be formed. By this method, a perfect thermosensitive liquid crystal display module can be obtained.

An embodiment of the present disclosure further provides a smart watch comprising the thermosensitive liquid crystal display module. For example, the smart watch comprises a dial and a watch band, and may further comprise such as watch band buckles. The watch band is provided with a built-in thermosensitive liquid crystal display module therein. The watch containing the above-mentioned thermosensitive liquid crystal display module may achieve the function of automatic human body temperature sensing without power consumption.

Figure 2:
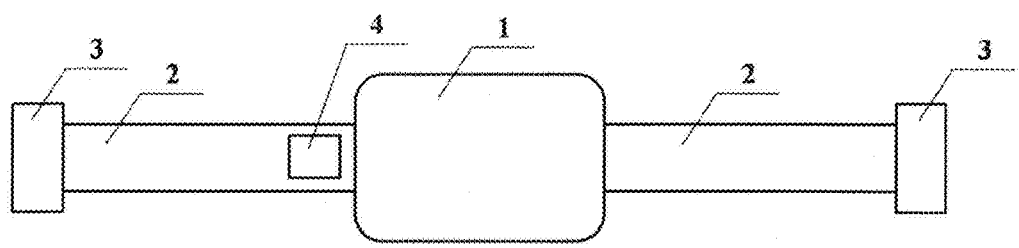
FIG. 2 is a structural schematic view of a smart watch band provided with the built-in thermosensitive liquid crystal display module on the left side of the dial.
Figure 3:
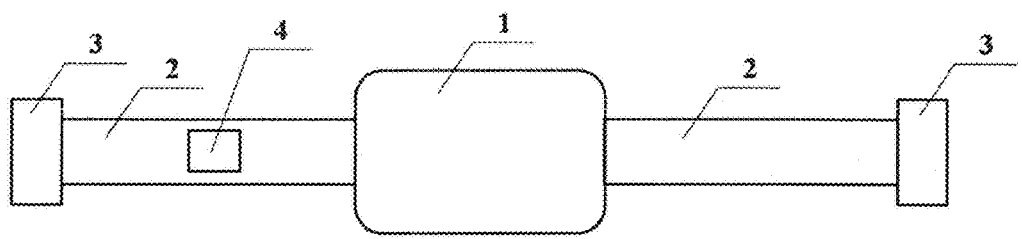
FIG. 3 is a structural schematic view of a smart watch band provided with the built-in thermosensitive liquid crystal display module on the middle thereof on the left side of the dial.
Figure 4:
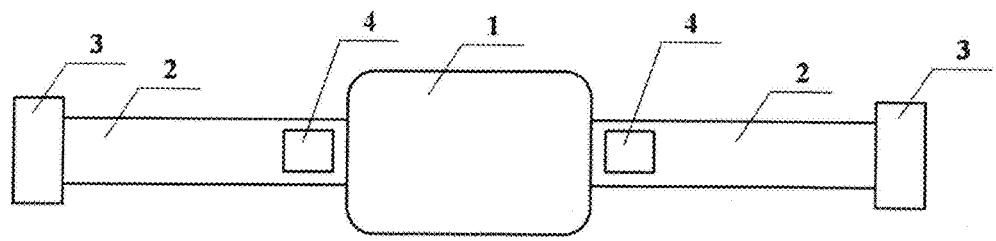
FIG. 4 is a structural schematic view of a smart watch band provided with the built-in thermosensitive liquid crystal display modules on both left and right sides of the dial.
Figure 5:
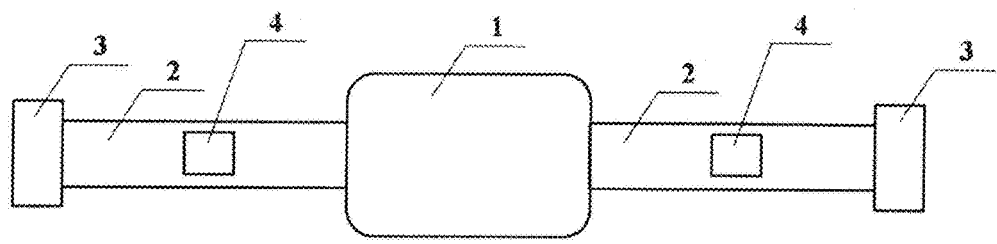
FIG. 5 is a structural schematic view of a smart watch band provided with the built-in thermosensitive liquid crystal display modules on the middle thereof on both left and right sides of the dial.

The number of the thermosensitive liquid crystal display modules is ≥1, and the thermosensitive liquid crystal display module(s) may be located at any position of the watch band, such as on the left side (as shown in FIG. 2) or right side of the watch band, and may also be located on both left and right sides of the watch band (as shown in FIGS. 4 and 5). Furthermore, the thermosensitive liquid crystal display module may be also located on the middle of the watch band (as shown in FIG. 3). The arrangement of the number of the thermosensitive liquid crystal display modules may further improve the automatic sensing sensitivity. The positions of the modules can also be adjusted randomly without influencing the overall design of the watch.

In the embodiment of the present disclosure, a crosslinking agent and a liquid crystalline monomer are grafted onto a polymethylhydrosiloxane backbone chain to obtain a cholesteric phase elastomer. The selective reflected wavelength thereof can be changed with temperature, thereby changing color thereof. The use of the thermosensitive liquid crystal display module prepared therefrom in a smart watch may achieve the function of automatic human body temperature sensing without power consumption.

The embodiments below are used for illustrating the present disclosure but not limiting the scope thereof.

Embodiment 1 A Polysiloxane Elastomer Containing a Liquid Crystal Lateral Chain

This embodiment provides a polysiloxane elastomer containing a liquid crystal lateral chain with a structure as shown in FIG. 1, which is obtained by grafting a crosslinking agent 423 and a liquid crystalline monomer 422 on the backbone chain 421 of polymethylhydrosiloxane 421 by hydrosilylation reaction, wherein the grafting ratio of the crosslinking agent to the liquid crystalline monomer grafted on the polymethylhydrosiloxane backbone chain is 1:3.

The crosslinking agent is binaphthyl diol p-alkenyloxybenzoate with the following structural formula:

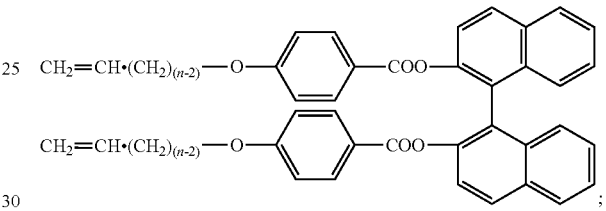

in the formula, n is 10.

The liquid crystalline monomer is cholesterol p-alkenyloxybenzoate with the following structural formula:

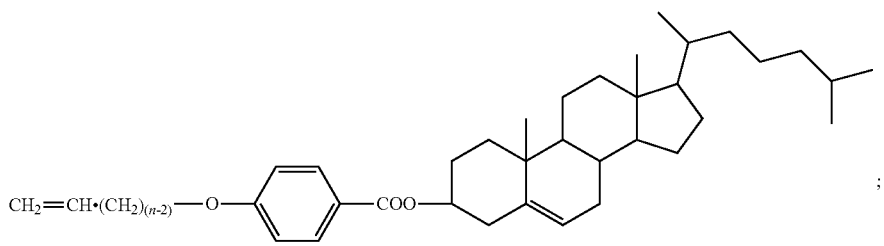

in the formula, n is 10.

The polymethylhydrosiloxane has the following structural formula:

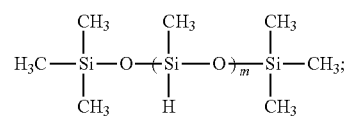

in the formula, m is 6.

The obtained polysiloxane elastomer containing a liquid crystal lateral chain has a glass transition temperature of 37° C. A cholesteric phase is displayed above the glass transition temperature. For example, the selective reflected wavelength thereof at 38° C. is 780 nm and therefore a red visible light may be displayed.

Embodiment 2 A Polysiloxane Elastomer Containing a Liquid Crystal Lateral Chain This embodiment provides a polysiloxane elastomer containing a liquid crystal lateral chain which is similar as that of embodiment 1 and differs therefrom in that:

1) the grafting ratio of the crosslinking agent to the liquid crystalline monomer grafted on the polymethylhydrosiloxane backbone chain is 1:1;
2) the crosslinking agent is binaphthyl diol p-alkenyloxybenzoate, wherein n is 8;
3) the liquid crystalline monomer is cholesterol p-alkenyloxybenzoate, wherein n is 8; and
4) in the polymethylhydrosiloxane, m is 8.

The obtained polysiloxane elastomer containing a liquid crystal lateral chain has a glass transition temperature of 30° C. A cholesteric phase is displayed above the glass transition temperature. For example, the selective reflected wavelength thereof at 37° C. is 1000 nm, which is outside the visible light range of 350-780 nm, therefore no color is reflected and a transparent state is displayed; and the selective reflected wavelength thereof at 38° C. is 750 nm and therefore a red color is reflected.

Embodiment 3 A Polysiloxane Elastomer Containing a Liquid Crystal Lateral Chain This embodiment provides a polysiloxane elastomer containing a liquid crystal lateral chain which is similar as that of embodiment 1 and differs therefrom in that:

1) the grafting ratio of the crosslinking agent to the liquid crystalline monomer grafted on the polymethylhydrosiloxane backbone chain is 1:2;
2) the crosslinking agent is binaphthyl diol p-alkenyloxybenzoate, wherein n is 12;
3) the liquid crystalline monomer is cholesterol p-alkenyloxybenzoate, wherein n is 12; and
4) in the polymethylhydrosiloxane, m is 10.

The obtained polysiloxane elastomer containing a liquid crystal lateral chain has a glass transition temperature of 28° C. A cholesteric phase is displayed above the glass transition temperature. For example, the selective reflected wavelength thereof at 37° C. is 750 nm and therefore a red color is displayed; and the selective reflected wavelength thereof at 38° C. is 620 nm and therefore a green color is reflected.

Embodiment 4 A Method for Preparing a Polysiloxane Elastomer Containing a Liquid Crystal Lateral Chain This embodiment provides the method for preparing the polysiloxane elastomer containing a liquid crystal lateral chain of embodiment 1: dissolving the polysiloxane into dried toluene; adding the crosslinking agent binaphthyl diol p-alkenyloxybenzoate and the liquid crystalline monomer cholesterol p-alkenyloxybenzoate; purging nitrogen gas for a while; adding chloroplatinic acid/tetrahydrofuran solution (1 g chloroplatinic acid in 150-300 ml tetrahydrofuran); reacting under reflux under nitrogen gas protection for 15-40 hours; pouring the reaction liquid into methanol; precipitating; filtering; washing with methanol, to obtain the polysiloxane elastomer containing a liquid crystal lateral chain.

The method described in embodiment 4 may be also used to obtain the polysiloxane elastomer containing a liquid crystal lateral chain of embodiments 2 and 3.

Embodiment 5 A Method for Preparing a Thermosensitive Liquid Crystal Display Module This embodiment provides a thermosensitive liquid crystal display module 4, as shown in FIG. 6, comprising a transparent thermal non-thermal-conductive material layer 41, a material layer 42 containing a polysiloxane elastomer containing a liquid crystal lateral chain, and a thermal conductive material layer 43, which are arranged from top to bottom. The transparent thermal non-thermal-conductive material protects the thermosensitive polysiloxane elastomer containing a liquid crystal lateral chain from the influence of the external temperature. Meanwhile, the color change of the polysiloxane elastomer containing a liquid crystal lateral chain can be sensed by human eyes. The thermal conductive material may transfer human body temperature to the thermosensitive polysiloxane elastomer containing a liquid crystal lateral chain to sense the body temperature and respond to the body temperature The transparent thermal non-thermal-conductive material layer is made of Teflon plastics and other materials. The thermal conductive material layer is made of at least one of those materials selected from thermal conductive silicon sheet, thermal conductive graphene and composite silicone oil thermal conductive grease. The thermosensitive liquid crystal display module is prepared by the following steps: arranging the material layer containing a polysiloxane elastomer containing a liquid crystal lateral chain on the surface of the thermal conductive material layer; covering with a transparent thermal non-thermal-conductive material layer; and forming into a shape by extruding.

Embodiment 6 A Smart Watch Band and a Watch Composed Thereof

This embodiment provides a smart watch, as shown in FIG. 4, comprising a dial 1, a watch band 2 and watch band buckles 3. One built-in thermosensitive liquid crystal display module 4 mentioned above is arranged on the middle of the watch band on the both sides of the dial, respectively. The color change warning of the thermosensitive liquid crystal display modules may achieve the function of automatic human body temperature sensing without power consumption.

At the same time, in order to increase the automatic sensing sensitivity and consider appearance design and other factors, the number of the thermosensitive liquid crystal display modules may be increased or the specific location of the thermosensitive liquid crystal display module may be adjusted as necessary.

The above description is merely exemplary embodiments of the present disclosure which are not used for limiting the scope of protection of the present disclosure which is, however, determined by the attached claims.

The present application claims the priority of the Chinese Patent Application No. 201510515754.5 submitted on Aug. 20, 2015, and the content disclosed in the above Chinese patent application is incorporated by reference as part of this application.

What is claimed is:

1. A method of sensing body temperature without power consumption using a polysiloxane elastomer, comprising the steps of transferring human body temperature to the polysiloxane elastomer, the polysiloxane elastomer containing a liquid crystal lateral chain, comprising a polysiloxane backbone chain and a lateral chain formed by a liquid crystalline monomer and connected with the polysiloxane backbone chain, wherein the polysiloxane backbone chain is crosslinked by a crosslinking agent;

the polysiloxane is polymethylhydrosiloxane, and the crosslinking agent and the liquid crystalline monomer are connected on the polysiloxane by hydrosilylation reaction;
the crosslinking agent is binaphthyl diol p-alkenyloxybenzoate with the following structural formula:

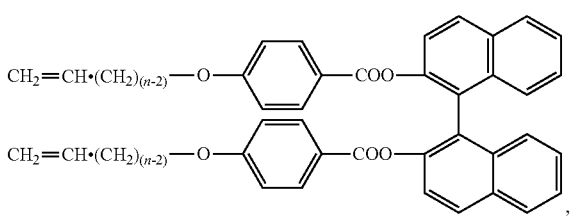

wherein n is an integer of 2-15;
the liquid crystalline monomer is cholesterol p-alkenyloxybenzoate with the following structural formula:

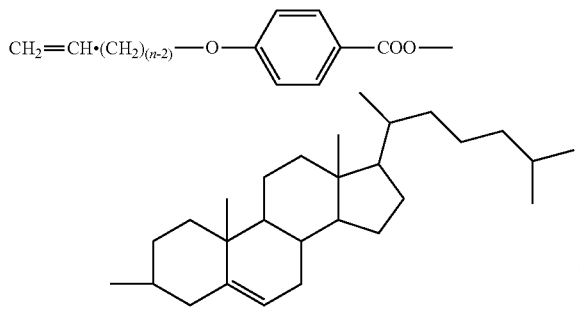

wherein n is an integer of 2-15;
the polymethylhydrosiloxane has the following structural formula:

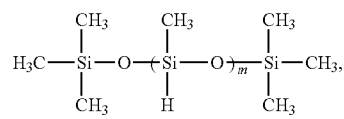

wherein m is an integer of 4-30;
wherein the number m of the Si—H bonds in the polymethylhydrosiloxane is 6; an olefin carbon chain length n in the liquid crystalline monomer is 10; an olefin carbon chain length n in the crosslinking agent is 10; and a grafting ratio of the crosslinking agent to the liquid crystalline monomer is 1:3;
the polysiloxane elastomer containing a liquid crystal lateral chain has a glass transition temperature of 37° C., and is in a cholesteric phase above the glass transition temperature.

2. A method of sensing body temperature without power consumption using a polysiloxane elastomer, comprising the steps of transferring human body temperature to the polysiloxane elastomer, the polysiloxane elastomer containing a liquid crystal lateral chain, comprising a polysiloxane backbone chain and a lateral chain formed by a liquid crystalline monomer and connected with the polysiloxane backbone chain, wherein the polysiloxane backbone chain is crosslinked by a crosslinking agent;

the polysiloxane is polymethylhydrosiloxane, and the crosslinking agent and the liquid crystalline monomer are connected on the polysiloxane by hydrosilylation reaction;
the crosslinking agent is binaphthyl diol p-alkenyloxybenzoate with the following structural formula:

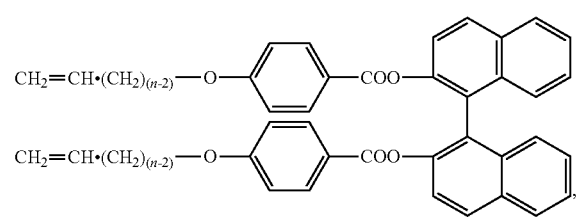

wherein n is an integer of 2-15;
the liquid crystalline monomer is cholesterol p-alkenyloxybenzoate with the following structural formula:

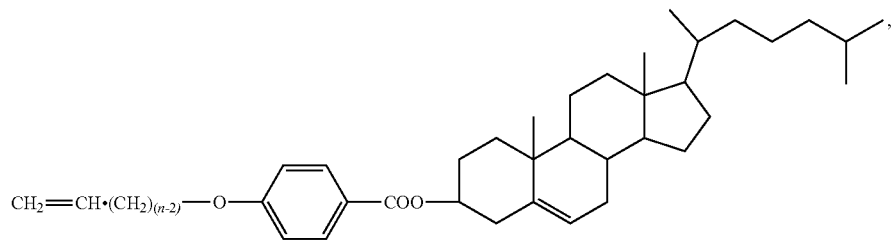

wherein n is an integer of 2-15;
the polymethylhydrosiloxane has the following structural formula:

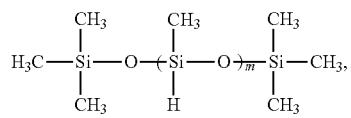

wherein m is an integer of 4-30;
wherein the number m of the Si—H bonds in the polymethylhydrosiloxane is 8; an olefin carbon chain length n in the liquid crystalline monomer is 8; an olefin carbon chain length n in the crosslinking agent is 8; and a grafting ratio of the crosslinking agent to the liquid crystalline monomer is 1:1;
the polysiloxane elastomer containing a liquid crystal lateral chain has a glass transition temperature of 30° C., and is in a cholesteric phase above the glass transition temperature.

3. A method of sensing body temperature without power consumption using a polysiloxane elastomer, comprising the steps of transferring human body temperature to the polysiloxane elastomer, the polysiloxane elastomer containing a liquid crystal lateral chain, comprising a polysiloxane backbone chain and a lateral chain formed by a liquid crystalline monomer and connected with the polysiloxane backbone chain, wherein the polysiloxane backbone chain is crosslinked by a crosslinking agent;
the polysiloxane is polymethylhydrosiloxane, and the crosslinking agent and the liquid crystalline monomer are connected on the polysiloxane by hydrosilylation reaction;
the crosslinking agent is binaphthyl diol p-alkenyloxybenzoate with the following structural formula:

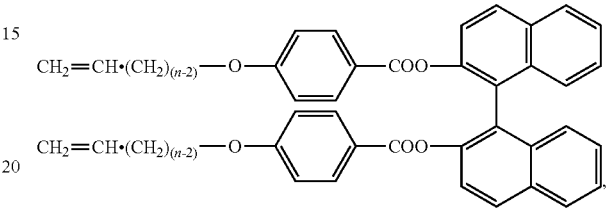

wherein n is an integer of 2-15;
the liquid crystalline monomer is cholesterol p-alkenyloxybenzoate with the following structural formula:

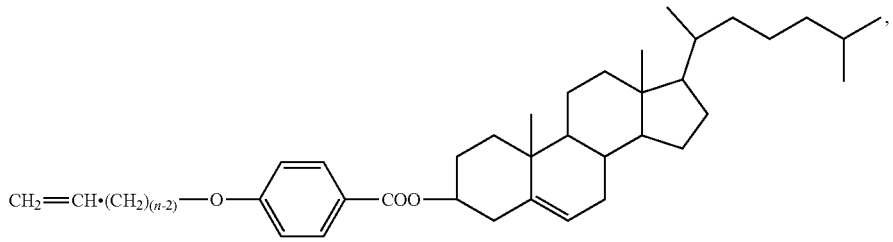

wherein n is an integer of 2-15;
the polymethylhydrosiloxane has the following structural formula:

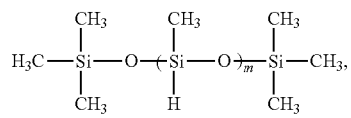

wherein m is an integer of 4-30;
wherein the number m of the Si—H bonds in the polymethylhydrosiloxane is 10; an olefin carbon chain length n in the liquid crystalline monomer is 12; an olefin carbon chain length n in the crosslinking agent is 12; and a grafting ratio of the crosslinking agent to the liquid crystalline monomer is 1:2;
the polysiloxane elastomer containing a liquid crystal lateral chain has a glass transition temperature of 28° C., and is in a cholesteric phase above the glass transition temperature.

* * * * *